United States Patent [19]

Graham et al.

[11] Patent Number: 4,851,546

[45] Date of Patent: Jul. 25, 1989

[54] PREPARATION OF PYRROLIDONES BY CATALYTIC HYDROGENATION OF MALEIMIDES

[75] Inventors: Anne M. Graham, Northfield; Thomas G. Attig, Aurora, both of Ohio

[73] Assignee: The Standard Oil Company, Cleveland, Ohio

[21] Appl. No.: 266,261

[22] Filed: Oct. 28, 1988

Related U.S. Application Data

[63] Continuation of Ser. No. 103,148, Oct. 1, 1987, abandoned.

[51] Int. Cl.$^4$ ............................................. C07D 207/12
[52] U.S. Cl. .................................... 548/543; 548/548; 548/545; 548/552
[58] Field of Search ................ 548/548, 552, 545, 543

[56] References Cited

U.S. PATENT DOCUMENTS

| | | | |
|---|---|---|---|
| 2,187,745 | 1/1940 | Lazier | 548/522 X |
| 3,092,638 | 6/1963 | Liao et al. | 548/552 |
| 3,397,210 | 8/1968 | Michalowicz | 548/548 |
| 3,681,387 | 8/1972 | Hollstein et al. | 548/552 |
| 4,356,124 | 10/1982 | Pesa et al. | 548/545 X |
| 4,515,965 | 5/1985 | Hupp | 548/548 |
| 4,520,206 | 5/1985 | Hupp | 548/548 |
| 4,721,789 | 1/1988 | DiCosimo et al. | 546/250 |
| 4,731,454 | 3/1988 | Otake et al. | 548/543 |

FOREIGN PATENT DOCUMENTS 209638  2/1983  Czechoslovakia .

OTHER PUBLICATIONS

Noller, "Chemistry of Organic Compounds", 1965, 3rd ed., pp. 94–95.
Polievka et al.; C.A.99:71288c (1983).

*Primary Examiner*—Joseph P. Brust
*Attorney, Agent, or Firm*—C. S. Lynch; D. J. Untener; L. W. Evans

[57] ABSTRACT

Disclosed is a process for making a 2-pyrrolidone and a succinimide by the vapor phase catalytic reaction of a maleimide with molecular hydrogen.

18 Claims, No Drawings

PREPARATION OF PYRROLIDONES BY CATALYTIC HYDROGENATION OF MALEIMIDES

This is a file wrapper continuation of application Ser. No. 103,148 filed Oct. 1, 1987, now abandoned.

This invention relates to the preparation of pyrrolidones by catalytic hydrogenation of maleimides.

Pyrrolidones are commercially prepared at present by a multi-step process based on acetylene. Formaldehyde is reacted catalytically with acetylene to produce 2-butyne-1,4-diol, which is reduced to 1,4-butanediol. This product is catalytically dehydrogenated to gamma-butyrolactone, which is converted to various pyrrolidones by reaction with ammonia or primary amines.

Butane is a less expensive starting material than acetylene. It is commercially converted to maleic anhydride at relatively low cost. Maleimides can be made by the liquid or vapor phase reaction with ammonia or primary amines, followed by cyclodehydration.

It is an object of the invention to provide a route for making 2-pyrrolidones from inexpensive butane-derived maleimides.

It is another object to provide a method for making 2-pyrrolidones by the catalytic reaction of maleimides with hydrogen.

Other objects, as well as aspects, features and advantages of the invention, will become apparent from a study of the specification, including illustrative examples.

According to the present invention there is provided a process for making a 2-pyrrolidone of the formula

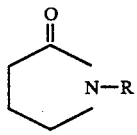

and a succinimide of the formula

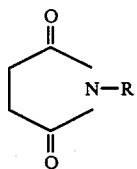

by the vapor phase reaction of a maleimide of the formula

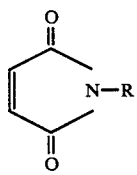

with molecular hydrogen, where R contains 0–8 carbon atoms, contains no carbon-to-carbon unsaturation and is H or is a hydrocarbyl group, or is a hydrocarbyl group substituted with one or more (usually one) hydroxyl groups.

Examples of such R groups are alkyl groups such as methyl, ethyl, hexyl, octyl, isopropyl, isobutyl, etc.; cycloalkyl groups such as cyclopentyl and cyclohexyl; alkylcycloalkyl groups and cycloalkylalkyl groups such as 2-methylcyclohexyl, 3-ethylcyclohexyl, 2-isopropylcyclopentyl, cyclohexylmethyl, cyclohexylethyl, cyclopentylpropyl, cyclopentylisobutyl and the like. Other examples are any of the above groups having any one of the hydrogen atoms substituted with an —OH group.

The process of the invention is especially useful where R is H or methyl or 2-hydroxyethyl or cyclohexyl, to make, respectively, 2-pyrrolidone or N-methyl-2-pyrrolidone, N-2-hydroxyethyl-2-pyrrolidone or N-cyclohexyl-2-pyrrolidone.

Thus, we have discovered the reaction of hydrogen with a maleimide to produce a 2-pyrrolidone and a succinimide. We regard this reaction per se as our invention since it is a completely new and unreported reaction. We have found that the reaction does not proceed to a detectable degree in the absence of a catalyst. We have found that the solid contact hydrogenation catalyst which is shown in the specific examples promotes the new reaction, as do copper, nickel or cobalt oxides, and ruthenium, platinum or palladium metals. Other untried hydrogenation catalysts may or may not be effective. However, since we have discovered an unexpected, unreported new reaction we regard the scope of our invention to be the vapor phase catalytic reaction of gaseous hydrogen with a maleimide to yield a corresponding 2-pyrrolidone and a corresponding succinimide, divorced from any designation of a specific catalyst.

Maleimide very easily undergoes homopolymerization when heated. We have discovered that the key to the successful hydrogenation of a maleimide to a 2-pyrrolidone and a succinimide is to contact the hydrogen, the substrate and the catalyst in the vapor phase. Failure to accomplish this objective results in heavy polymerization, thus preempting the hydrogenation reaction to the desired product, particularly since the polymer coats the catalyst and makes it unavailable to the reactants.

Suitable process conditions include 150° to 350° C. (usually 150°–250° C.), 200 to 1800 psia, a molar ratio of $H_2$ to maleimide in the range from 10 to 600 and a contact time in the range from 0.3 seconds to 300 minutes. Higher pressures can also be used. It will be understood that contact time and temperature have an inverse relationship. More usually contact times are in the range from 10 seconds to 10 minutes.

One technique for accomplishing contact of hydrogen, catalyst and the substrate while the maleimide reactant is in the vapor phase is the procedure used in the specific examples herein. Thus, the solid maleimide compound substrate can be dissolved in a solvent which does not interfere with the main reaction, e.g., dioxane, methanol ethanol dimethylacetamide, N-methyl-2-pyrrolidone, and then the solution can be heated to vaporize the substrate (and part or all of the solvent) while passing the hydrogen into admixture with the vapors of the substrate, the combined vapors then being passed over the hot catalysts. The solvent is for convenience and is not necessary. Thus, alternatively, a solid maleimide can be vaporized (melted and vaporized or sublimed), mixed with $H_2$ and passed over the heated catalyst under suitable reaction conditions.

The foregoing reaction conditions and techniques are not regarded as a part of the broad invention, which is the reaction itself, as previously noted.

The succinimide product of our process can be taken as a primary product or, if desired, further hydrogenated in a separate step to yield further 2-pyrrolidones.

The following specific examples of the invention are illustrative only and are not to be considered as in any way limiting.

EXAMPLE 1

150 cc of 10/30 mesh alumina was dried four hours at 125° C. A solution was made as follows: 9.12 g of Fe(NO$_3$)$_3$·9H$_2$O and 6.54 g of Ni(NO$_3$)$_2$·6H$_2$O were added to 56.88 g of Ru(NO$_3$)$_3$ which had been diluted to a total of 75 g with water. The alumina was impregnated with this solution using the incipient wetness technique. The application of the Fe—Ni—Ru was done in two steps, with drying after addition of the first portion of the solution. After the second wetting or impregnation, the catalyst composition was dried overnight at 125° C. and then calcined for 3 hours at 350° C. Before using a portion of the catalyst in any run, it was reduced by contact with flowing H$_2$ gas overnight at 250° C.

EXAMPLE 2

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of H$_2$ at 250° C. for 15 hours. Then a 1.8 weight percent solution of maleimide in dioxane was fed by high pressure syringe pump into the top of the preheat zone, together with hydrogen gas. The molar ratio of H$_2$ to maleimide was 297, the temperature was 175° C., the pressure was 1300 psia, and the contact time was 2.1 minutes. After about 5 hours pre-run, the product was passed through a room temperature condenser and the collected liquid was analyzed by gas chromatography. Conversion was 100 percent and the yield of 2-pyrrolidone was 31.6% and the yield of succinimide was 51.6%, based on the maleimide fed.

EXAMPLE 3

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of H$_2$ at 250° C. for 15 hours. Then a 5 weight percent solution of N-methylmaleimide in dioxane was fed by high pressure syringe pump into the top of the preheat zone, together with hydrogen gas. The molar ratio of H$_2$ to maleimide was 297, the temperature was 175° C., the pressure was 1300 psia, and the contact time was 2.1 minutes. After about 5 hours pre-run, the product was passed through a room temperature condenser for 85 minutes and the collected liquid was analyzed by gas chromatography. Conversion was 100 percent and the yield of N-methyl-2-pyrrolidone was 53.2% and the yield of succinimide was 38.8%, based on the N-methylmaleimide fed.

EXAMPLE 4

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of H$_2$ at 250° C. for 15 hours. Then a 1.8 weight percent solution of maleimide in dioxane was fed by high pressure syringe pump into the top of the preheat zone, together with hydrogen gas. The molar ratio of H$_2$ to maleimide was 297, the temperature was 150° C., the pressure was 1300 psia, and the contact time was 2.2 minutes. After about 5 hours pre-run, the product was passed through a room temperature condenser for 46 minutes and the collected liquid was analyzed by gas chromatography. Conversion was 100 percent and the yield of 2-pyrrolidone was 12% and the yield of succinimide was 92%, based on the maleimide fed. The analyzed value obtained for succinimide is somewhat high when the yield is very high, as here.

As will be evident to those skilled in the art various modifications of this invention can be made or followed in the light of the foregoing disclosure and discussion without departing from the spirit and scope of the disclosure or from the scope of the claims.

We claim:

1. A process for making a 2-pyrrolidone of the formula

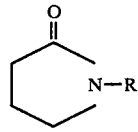

and a succinimide of the formula

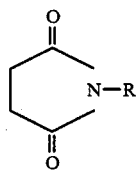

by the vapor phase catalytic reaction of a maleimide of the formula

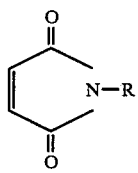

with molecular hydrogen, where R contains 0–8 carbon atoms, contains no carbon-to-carbon unsaturation an is H or is a hydrocarbyl group, or is a hydrocarbyl group substituted with one or more hydroxyl groups.

2. A process of claim 1 wherein said reaction is effected at temperatures in the range from 150° to 350° C.

3. A process of claim 1 wherein said reaction is effected at temperatures in the range from 150° to 250° C.

4. A process of claim 1 wherein the molar ratio of hydrogen reactant to the maleimide reactant of formula (3) is in the range from 10 to 600 and the pressure is in the range from 200 to 1800 psia.

5. A process of claim 2 wherein the molar ratio of hydrogen reactant to the maleimide reactant of formula (3) is in the range from 10 to 600 and the pressure is in the range from 200 to 1800 psia.

6. A process of claim 3 wherein the molar ratio of hydrogen reactant to the maleimide reactant of formula (3) is in the range from 10 to 600 and the pressure is in the range from 200 to 1800 psia.
7. A process of claim 1 where R is H.
8. A process of claim 2 where R is H.
9. A process of claim 3 where R is H.
10. A process of claim 4 where R is H.
11. A process of claim 5 where R is H.
12. A process of claim 6 where R is H.
13. A process of claim 1 where R is methyl.
14. A process of claim 2 where R is methyl.
15. A process of claim 3 where R is methyl.
16. A process of claim 4 where R is methyl.
17. A process of claim 5 where R is methyl.
18. A process of claim 6 where R is methyl.

* * * * *